(12) United States Patent
Wang et al.

(10) Patent No.: US 10,336,615 B2
(45) Date of Patent: Jul. 2, 2019

(54) TITANIUM LIGAND-MODIFIED BLACK PHOSPHORUS AND PREPARATION METHOD AND USE THEREOF

(71) Applicant: Shenzhen Institutes of Advanced Technology, Shenzhen, Guangdong (CN)

(72) Inventors: Huaiyu Wang, Guangdong (CN); Yuetao Zhao, Guangdong (CN); Xuefeng Yu, Guangdong (CN)

(73) Assignee: SHENZHEN INSTITUTES OF ADVANCED TECHNOLOGY, Shenzhen, Guangdong (CN)

( * ) Notice: Subject to any disclaimer, the term of this patent is extended or adjusted under 35 U.S.C. 154(b) by 80 days.

(21) Appl. No.: 15/389,666

(22) Filed: Dec. 23, 2016

(65) Prior Publication Data

US 2017/0174516 A1    Jun. 22, 2017

Related U.S. Application Data

(63) Continuation of application No. PCT/CN2015/098879, filed on Dec. 25, 2015.

(30) Foreign Application Priority Data

Dec. 18, 2015  (CN) .......................... 2015 1 0956724

(51) Int. Cl.
*C01B 25/00* (2006.01)
*A61K 41/00* (2006.01)
(Continued)

(52) U.S. Cl.
CPC ........ *C01B 25/006* (2013.01); *A61K 41/0052* (2013.01); *A61K 41/0057* (2013.01);
(Continued)

(58) Field of Classification Search
None
See application file for complete search history.

(56) References Cited

U.S. PATENT DOCUMENTS

2010/0041895 A1\* 2/2010 Robinson ................ C07F 5/027
548/110

FOREIGN PATENT DOCUMENTS

CN          105116034 A       12/2015

OTHER PUBLICATIONS

Lee, H. U. et al., "Stable semiconductor black phosphorus (BP)@titanium dioxide (TiO2) hybrid photocatalysts," Scientific Reports, Mar. 3, 2015, vol. 5 : 8691, pp. 1-6.
(Continued)

*Primary Examiner* — Jeffrey D Washville
(74) *Attorney, Agent, or Firm* — Hamre, Schumann, Mueller & Larson, P.C.

(57) ABSTRACT

The present invention provides a titanium ligand-modified black phosphorus and the preparation method and use thereof. The titanium ligand-modified black phosphorus is a complex of black phosphorus and a titanium ligand having a structure represented by formula (I):

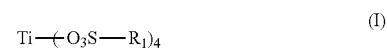

wherein in the formula (I), $R_1$ comprises $C_1$-$C_6$ alkyl, or phenyl optionally further substituted with 0 to 5 groups each independently selected from halogen atom, $C_1$-$C_6$ alkyl, nitro, hydroxy, amino or $C_1$-$C_3$ alkoxy; the $C_1$-$C_6$ alkyl or $C_1$-$C_3$ alkoxy is optionally further substituted with 0 to 3 groups each independently selected from halogen atom, nitro, hydroxy, amino, methyl, ethyl or n-propyl. The tita- (Continued)

nium ligand-modified black phosphorus of the present invention is not likely oxidized without changing inherent properties of the black phosphorus, and the antioxidant capacity is greatly enhanced.

26 Claims, 4 Drawing Sheets

(51) Int. Cl.
| | |
|---|---|
| H01L 51/00 | (2006.01) |
| C07F 9/06 | (2006.01) |
| C09K 15/14 | (2006.01) |
| C09K 15/28 | (2006.01) |
| C07C 309/04 | (2006.01) |
| C07C 309/06 | (2006.01) |
| C07C 309/29 | (2006.01) |
| C07C 309/30 | (2006.01) |
| C07C 309/39 | (2006.01) |
| C07C 309/40 | (2006.01) |
| C07C 309/42 | (2006.01) |
| C07C 309/46 | (2006.01) |
| H01L 51/05 | (2006.01) |
| H01L 51/50 | (2006.01) |

(52) U.S. Cl.
CPC .......... *C07C 309/04* (2013.01); *C07C 309/06* (2013.01); *C07C 309/29* (2013.01); *C07C 309/30* (2013.01); *C07C 309/39* (2013.01); *C07C 309/40* (2013.01); *C07C 309/42* (2013.01); *C07C 309/46* (2013.01); *C07F 9/06* (2013.01); *C09K 15/14* (2013.01); *C09K 15/28* (2013.01); *H01L 51/0084* (2013.01); *H01L 51/0558* (2013.01); *H01L 51/5012* (2013.01)

(56) References Cited

OTHER PUBLICATIONS

Kim, J. S. et al., "Toward air-stable multilayer phosphorene thin-films and transistors," Scientific Reports, Mar. 11, 2015, vol. 5 : 8989, pp. 1-7.
Wood, J. D. et al., "Effective Passivation of Exfoliated Black Phosphorus Transistors against Ambient Degradation," Nano Letters, Nov. 7, 2014, vol. 14, pp. 6964-6970.
Avsar, A. et al., "Electrical characterization of fully encapsulated ultra thin black phosphorus-based heterostructures with graphene contacts," arXiv.org, e-Print Archive, Condensed Matter, Dec. 3, 2014, pp. 1-32.
Churchill, H. O. H. et al., "Phosphorus joins the family," Nature Nanotechnology, May 2014, vol. 9, pp. 330-331.
Li, L. et al., "Black phosphorus field-effect transistors," Nature Nanotechnology, May 2014, vol. 9, pp. 372-377.
Qiao, J. S. et al., "High-mobility transport anisotropy and linear dichroism in few-layer black phosphorus," Nature Communications, Jul. 21, 2014, vol. 5:4475, pp. 1-7.
Xiang, D. et al., "Surface transfer doping induced effective modulation on ambipolar characteristics of few-layer black phosphorus," Nature Communications, Mar. 12, 2015, vol. 6:6485, pp. 1-8.
Wang, X. M. et al., "Highly anisotropic and robust excitons in monolayer black phosphorus," Nature Nanotechnology, Jun. 2015, vol. 10, pp. 517-521.
Sun, J. et al., "A phosphorene-graphene hybrid material as a high-capacity anode for sodium-ion batteries," Nature Nanotechnology, Nov. 2015, vol. 10, pp. 980-985.
Favron, A. et al., "Photooxidation and quantum confinement effects in exfoliated black phosphorus," Nature Materials, Aug. 2015, vol. 14, pp. 826-832.
International Search Report issued for counterpart PCT Application No. PCT/CN2015/098879, dated Jul. 4, 2016, 8 pages including English translation.
First Office Action issued for counterpart Chinese Patent Application No. 201510956724.8, dated Apr. 20, 2017, 7 pages including English translation.
Search Report issued for counterpart Chinese Patent Application No. 201510956724.8, dated Apr. 20, 2017, 6 pages including English translation.
Churchill et al., "Phosphorus joins the family", Nature Nanotechnology, vol. 9, May 2014, pp. 330-331 (cited on p. 1 of the specification).
Li et al., "Black phosphorus field-effect transistors", Nature Nanotechnology, vol. 9, May 2014, pp. 372-377, can be found at http://www.nature.com/nnano/journal/v9/n5/full/nnano.2014.35.html (cited on p. 1 of the specification).
Qiao et al., "High-mobility transport anisotropy and linear dichroism in few-layer black phosphorus", Nature Communications, Jul. 21, 2014, pp. 1-7 (cited on p. 1 of the specification).
Xiang et al., "Surface transfer doping induced effective modulation on ambipolar characteristics of few-layer black phosphorus" Nature Communications, Mar. 12, 2015, pp. 1-8 (cited on p. 1 of the specification).
Wang et al., "Highly anisotropic and robust excitons in monolayer black phosphorus", Nature Nanotechnology, vol. 10, Jun. 2015, pp. 517-521 (cited on p. 1 of the specification).
Sun et al., "A phosphorene-graphene hybrid material as a high-capacity anode for sodium-ion batteries", Nature Nanotechnology, vol. 10, Nov. 2015, pp. 980-986, can be found at http://www.nature.com/nnano/journal/v10/n11/full/nnano.2015.194.html (cited on p. 1 of the specification).
Favron et al., "Photooxidation and quantum confinement effects in exfoliated black phosphorus", Nature Materials, vol. 14, Aug. 2015, pp. 826-833, can be found at http://www.nature.com/nmat/journal/v14/n8/full/nmat4299.html (cited on p. 2 of the specification).
Wood et al., "Effective Passivation of Exfoliated Black Phosphorus Transistors against Ambient Degradation", Nano Lett., vol. 14, Nov. 7, 2014, pp. 6964-6970 (cited on p. 2 of the specification).
Kim et al., "Toward air-stable multilayer phosphorene thin-films and transistors", Scientific Reports, Mar. 11, 2015, pp. 1-7 (cited on p. 2 of the specification).
Lee et al., "Stable semiconductor black phosphorus (BP)@titanium dioxide (TiO2) hybrid photocatalysts", Scientific Reports, Mar. 3, 2015, pp. 1-6 (cited on p. 2 of the specification).

* cited by examiner

TITANIUM LIGAND-MODIFIED BLACK PHOSPHORUS AND PREPARATION METHOD AND USE THEREOF

FIELD OF THE INVENTION

The present invention relates to black phosphorus and the preparation method and use thereof, and particularly, to a titanium ligand-modified black phosphorus and the preparation method and use thereof.

BACKGROUND OF THE INVENTION

Two-dimensional materials are research hotspots in recent years, and typical representatives include graphene and transition metal disulfides having semiconducting properties. A new two-dimensional material, black phosphorus, has appeared since 2013. Black phosphorus (BP) is a new form of elemental phosphorus generated from the reaction of white phosphorus under high temperature and high pressure. Different from white phosphorus having a tetrahedral crystal structure composed of four phosphorus atoms, the crystal structure of black phosphorus is rearranged under high temperature and high pressure, so that a great number of phosphorus atoms are connected with each other to form a regularly arranged planar structure (H. O. Churchill, P. Jarillo-Herrero. *Nat. Nanotechnol.* 2014, 9, 330). In this plane, each phosphorus atom is connected to the other three phosphorus atoms, and has a certain bond length and bond angle; the planes are stacked together by van der Waals force. This especial arrangement allows the black phosphorus to have better stability (white phosphorus and red phosphorus are likely to undergo spontaneous combustion in air, while black phosphorus is not like that) and more unique physical, chemical, biological and other properties, for example, variable band gap energy and good carrier mobility.

Like graphene, black phosphorus has excellent performances in mechanics, electronics, optics, thermotics, acoustics, and the like. Due to these properties, the study on black phosphorus is exploding in the past two years (H. O. Churchill, P. Jarillo-Herrero. *Nat. Nanotechnol.* 2014, 9, 330. L. Li, Y. Yu, et al. *Nat. Nanotechnol.* 2014, 9, 372. J. S. Qiao, X. H. Kong, et al. *NatureCommun.* 2014, 5,4475. D. Xiang, C. Han, et al. *Nature Commun.* 2014, 6, 6485. X. M. Wang, A. M. Jones, et al. *Nanotechnol.* 2015, 10, 517. J. Sun, H. W. Lee, et al. *Nat. Nanotechnol.* 2015).

Although black phosphorus has better stability than white phosphorus and red phosphorus, it still tends to be slowly oxidized by oxygen in water or air, thereby affecting its structure and function. Currently, the mechanism for which black phosphorus is oxidized has been clarified: phosphorus atom tends to react with oxygen to generate oxides of phosphorus, which in turn react with moisture in air to generate phosphoric acid (A. Favron, E. Gaufrès, et al. *Nature Mater.* 2015, 14, 826). The whole process will cause damage to the structure of black phosphorus, so that it would lose performance in electronics, optics, and the like. Therefore, how to solve the problem of black phosphorus susceptible to oxidation and to maintain the stability of structure and performance thereof becomes a key issue in the development of black phosphorus.

In order to solve the problem of oxidation of black phosphorus, various substances are coated onto the surface of black phosphorus in different ways by researchers, so as to block oxygen and moisture and reduce the opportunities of exposure of phosphorus atoms to oxygen and moisture: Wood et al. places black phosphorus on a silicon-based surface, and covers the upper surface of black phosphorus with oxides of titanium, gold and aluminum successively, so that the stability of black phosphorus is enhanced (J. D. Wood, S. A. Wells, et al. *Nano Lett.* 2014, 14, 6964); kim et al. places black phosphorus on the surface of $Al_2O_3$, and meanwhile covers the upper surface of black phosphorus with a layer of $Al_2O_3$, so that only the phosphorus atoms on the lateral side can expose to oxygen atoms, but the number of phosphorus atoms on the lateral side is quite small as compared with that of the upper and lower surfaces, and thus the antioxidant capacity of black phosphorus can be greatly enhanced (J. S. Kim, Y. Liu, et al. *Sci. Rep.* 2015, 5, 8989); Lee et al. deposits nanoscale titanium dioxide on the surface of black phosphorus by an atomic deposition process, so that the stability of black phosphorus can also be improved (H. U. Lee, S. C. Lee, et al. *Sci. Rep.* 2015, 5, 8691).

The core idea in the existing solutions is to coat other substances on the surface of black phosphorus to reduce the exposure of black phosphorus to oxygen and moisture, but its effect of eliminating the oxidization of black phosphorus is not satisfactory. Therefore, there is a need to find a new solution to eliminate the oxidation of black phosphorus.

SUMMARY OF THE INVENTION

An object of the present invention is to provide a new titanium ligand-modified black phosphorus which can maintain the stability of structure and performance of black phosphorus and enhance the antioxidant capacity of black phosphorus.

Another object of the present invention is to provide a method of producing the titanium ligand-modified black phosphorus.

Yet another object of the present invention is to provide use of the titanium ligand-modified black phosphorus.

In order to achieve the above objects, in one aspect, the present invention provides a titanium ligand-modified black phosphorus, which is a complex of black phosphorus and a titanium ligand having a structure represented by formula (I):

wherein in the formula (I), $R_1$ comprises $C_1$-$C_6$ alkyl, or phenyl optionally further substituted with 0 to 5 groups each independently selected from halogen atom, $C_1$-$C_6$ alkyl, nitro, hydroxy, amino or $C_1$-$C_3$ alkoxy; the $C_1$-$C_6$ alkyl or $C_1$-$C_3$ alkoxy is optionally further substituted with 0 to 3 groups each independently selected from halogen atom, nitro, hydroxy, amino, methyl, ethyl or n-propyl.

Preferably, the $C_1$-$C_6$ alkyl is $C_1$-$C_3$ alkyl.

The $C_1$-$C_6$ alkyl in the present invention refers to a straight or branched alkyl having 1 to 6 carbon atoms, including, but not limited to, methyl, ethyl, n-propyl, isopropyl, n-butyl, isobutyl, t-butyl, n-pentyl, isopentyl, sec-pentyl, neopentyl, n-hexyl, isohexyl, and the like.

The $C_1$-$C_3$ alkyl in the present invention refers to a straight or branched alkyl having 1 to 3 carbon atoms, including methyl, ethyl, n-propyl, isopropyl.

The halogen in the present invention includes fluorine, chlorine, bromine or iodine, and fluorine is preferable.

Preferably, the titanium ligand as shown in the formula (I) comprises:

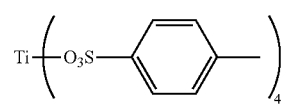
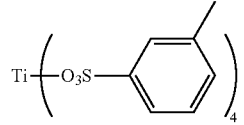
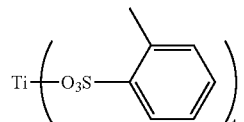
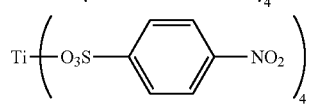
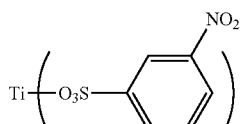
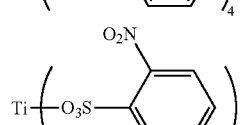
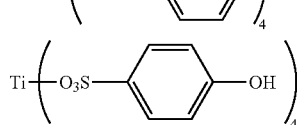
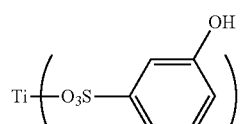
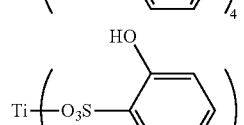
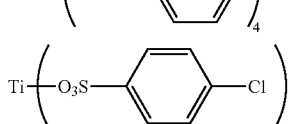
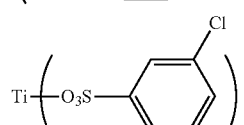
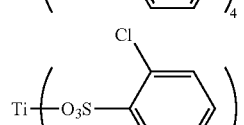
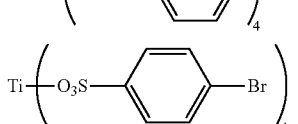
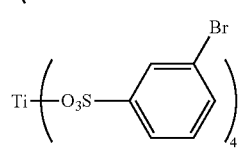
-continued
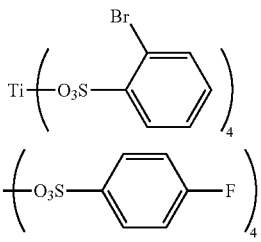
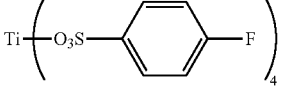
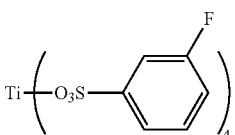
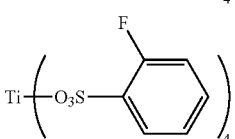
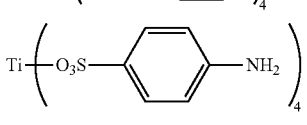
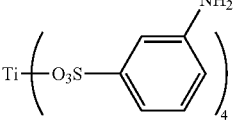
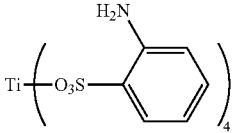
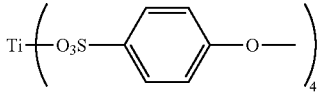
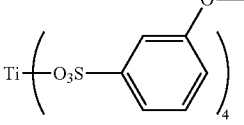
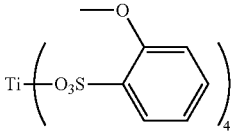
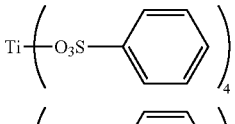
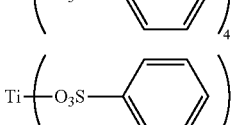
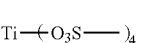
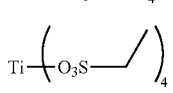

-continued

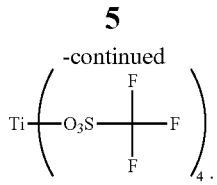

As analyzed above, black phosphorus is unstable in water or air, and may be easily oxidized to generate oxides of phosphorous and phosphoric acid, leading to the disintegration of structure and the disappearance of performance in black phosphorus. Upon analysis, the present invention considers that the reason why black phosphorus tends to react with oxygen lies in that after a phosphorus atom bonds to other three phosphorus atoms, there remains a pair of lone pair electrons on the outer layer, which may be easily taken away by oxygen molecules, resulting in oxidation of black phosphorus. The prior art does not solve the problem of oxidation of black phosphorus from the viewpoint of lone pair electrons, and the lone pair electrons still exist when oxides of titanium, gold and aluminum are used on the black phosphorus surface, so that black phosphorus is still likely to be oxidized. Starting from the lone pair electrons, the present invention designs a ligand that can bond to the lone pair electrons and occupy the electrons so that they cannot bond to oxygen, and effectively solves the problem of reaction of black phosphorus with oxygen based on the lone pair electrons.

Starting from the lone pair electrons of phosphorus atom in black phosphorus, the present invention designs a novel metal ligand, titanium sulfonate, which uses the empty orbit on a titanium atom to coordinate with the lone pair electrons of a phosphorus atom to form a stable coordination bond, so as to achieve the purpose of stabilizing the lone pair electrons of the phosphorus atom. Experiments shows that the titanium sulfonate as shown in formula (I) of the present invention can form a complex with black phosphorus, and the resultant titanium ligand-modified black phosphorus of the present invention is not likely oxidized without changing inherent properties of the black phosphorus, and the antioxidant capacity is greatly enhanced.

In accordance with a specific embodiment of the present invention, in the titanium ligand-modified black phosphorus according to the present invention, the black phosphorus comprises one or more of black phosphorous bulk material, multilayered black phosphorous nanosheet, monolayer black phosphorous nanosheet and black phosphorus quantum dot.

The multilayered black phosphorous nanosheet refers to a black phosphorus nanosheet having two or more atomic layers and a thickness of less than 100 nm.

In the present invention, the black phosphorous bulk material refers to a black phosphorous bulk material that is not exfoliated.

In the present invention, the monolayer black phosphorous nanosheet refers to a black phosphorous nanosheet having a thickness of a single atomic layer.

In the present invention, the black phosphorus quantum dot refers to a black phosphorus nanoparticle having a hydrodynamic particle size of less than 10 nm.

In another aspect, the present invention provides a method of producing the titanium ligand-modified black phosphorus, comprising the steps of:

providing the titanium ligand and the black phosphorus in an organic solvent to take place a reaction protected from light under an inert condition to obtain the titanium ligand-modified black phosphorus; preferably, the titanium ligand and the black phosphorus are at a molar ratio of between 0.9:1 and 10:1, more preferably between 3:1 and 10:1.

Preferably, in the method according to the present invention, the organic solvent comprises polar solvent and/or non-polar solvent, and the polar solvent comprises polar protic solvent and/or polar aprotic solvent.

Preferably, the polar aprotic solvent comprises one or more of N-methylpyrrolidone, N, N-dimethylformamide, N,N-diethylformamide, N, N-dimethylacetamide, dimethylsulfoxide, tetrahydrofuran, ethyl acetate and acetone.

Preferably, the polar protic solvent comprises one or more of methanol, ethanol, n-propanol, isopropanol, ethylene glycol and butylene glycol;

Preferably, the non-polar solvent comprises methylene chloride and/or trichloromethane.

Preferably, in the method according to the present invention, the reaction is carried out at 4 to 45° C. for 12 to 24 h.

The titanium sulfonate as represented by formula (I) of the present invention can be effectively coordinated with black phosphorus by using the method as described above, so as to form the titanium ligand-modified black phosphorus according to the present invention.

In yet another aspect, the present invention provides a composition comprising the titanium ligand-modified black phosphorus according to the present invention.

In yet another aspect, the present invention provides use of the titanium ligand-modified black phosphorus or the composition in the preparation of a thin film transistor material, a negative electrode material for battery, a flexible display material, a LED material, an optical switch material, or a biosensor material.

In yet another aspect, the present invention provides use of the titanium ligand-modified black phosphorus or the composition in the preparation of photodynamic therapeutic agent or photothermal therapeutic agent for killing cancer cells.

The thin film transistor material in the present invention refers to a material for constituting thin film transistor semiconductor layer.

The negative electrode material for battery in the present invention refers to a raw material for forming the negative electrode in a battery.

The flexible display material in the present invention refers to a soft, deformable and flexible material for preparing a flexible display device.

The LED material in the present invention refers to a semiconductor material for constituting the basic structure of a light emitting diode.

The optical switch material in the present invention refers to a semiconductor material that can realize optical signal physical switching or logical operation in an optical transmission line or an integrated optical path.

The photodynamic therapeutic agent in the present invention refers to a material having a photodynamic effect. Photodynamic effect is a photosensitization reaction, accompanied with biological effects, involving oxygen molecules. The process is that the photosensitizer absorbed by a tissue is excited by irradiation with laser of a specific wavelength, and the photosensitizer at an excited state in turn transfers energy to the surrounding oxygen, to generate highly reactive singlet oxygen, which is subjected to an oxidation reaction with adjacent biomacromolecules, resulting in cytotoxic effect and thus damage and even death of cells.

The photothermal therapeutic agent in the present invention refers to a material used in the photothermal therapy, which is a material having high photothermal conversion efficiency. In use, this material is injected into a human body, accumulates in the vicinity of tumor tissues, and converts light energy into thermal energy under the irradiation from an external light source to perform treatment, such as killing cancer cells.

The biosensor material in the present invention refers to a material which is sensitive to biological substance and can convert its concentration into an electrical or optical signal for detection.

In conclusion, the present invention mainly provides a titanium ligand-modified black phosphorus, which is a complex of black phosphorus and a titanium ligand represented by formula (I), and the preparation method thereof. The titanium ligand-modified black phosphorus is not likely oxidized without changing inherent properties of the black phosphorus, and the antioxidant capacity is greatly enhanced.

DETAILED DESCRIPTION OF THE INVENTION

In order to understand the technical features, objects and beneficial effects of the present invention more clearly, the technical solution of the present invention will be described below in details with reference to specific examples and the accompanying drawings. It is understood that the examples intends to illustrate the present invention only, and are not intended to limit the scope of the invention.

EXAMPLE 1

A titanium ligand (TiL$_4$, L: p-toluenesulfonate group) used in this example is synthesized by the following route:

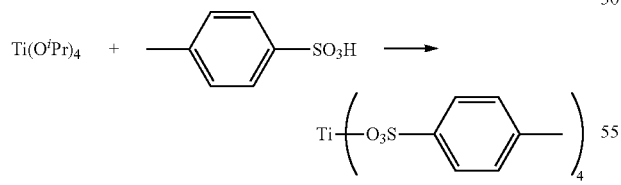

Figure 1:
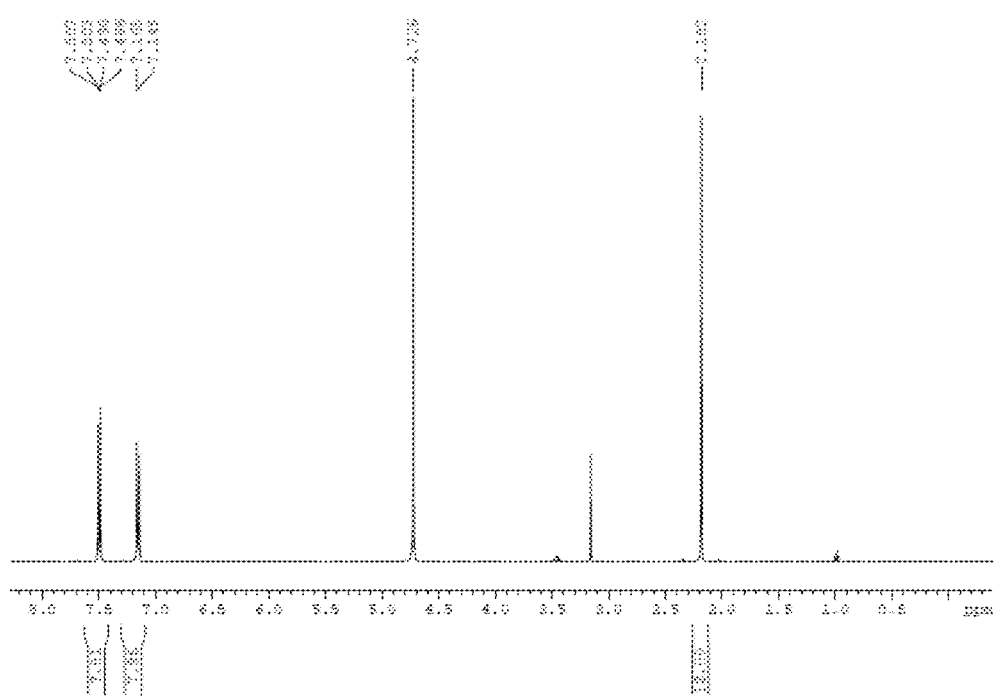
FIG. 1 is a $^1$H-NMR spectrum of the titanium ligand (TiL$_4$, L: p-toluenesulfonate group) produced in Example 1.

1.42 g of p-toluenesulfonic acid is dissolved in 10 mL of ethanol, and 5 mL of a solution of titanium tetraisopropoxide in ethanol having a concentration of 3.44 g/mL is slowly added dropwise thereto at 50° C. and stirred at 40 to 70° C. for 1 to 3 hours, followed by cooling to room temperature. The solvent is removed by rotary evaporation, and the remaining solid is titanium p-toluenesulfonate (TiL$_4$, L: p-toluenesulfonate group). $^1$H-NMR (D$_2$O) thereof is shown in the following FIG. 1.

Black phosphorus is modified with the obtained titanium p-toluenesulfonate as described above by the following route, where BP represents black phosphorus, P represents phosphorus atom, the colon ":" represents lone pair electrons, and BP's P means the phosphorus atom on black phosphorus:

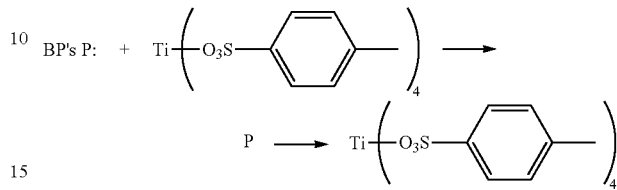

Figure 2:
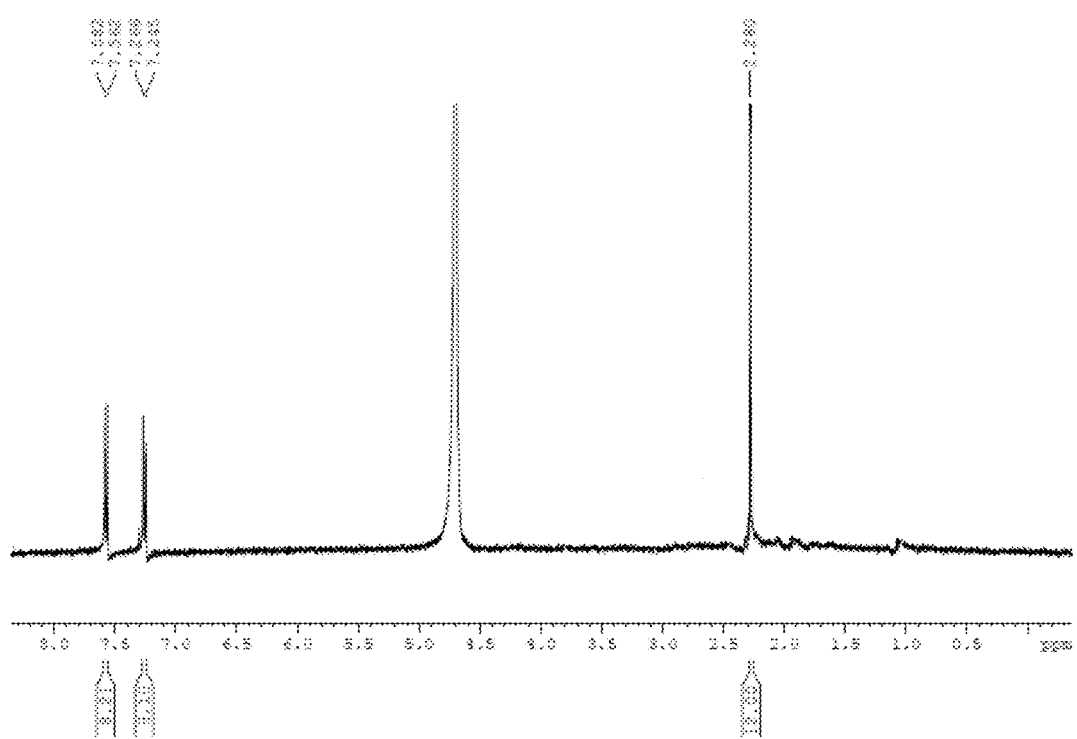
FIG. 2 is a $^1$H-NMR spectrum of the titanium ligand (TiL$_4$, L: p-toluenesulfonate group)-modified black phosphorus produced in Example 1.

10.8 mg of titanium p-toluenesulfonate (TiL$_4$, L: p-toluenesulfonate group) is dissolved in 1 mL of NMP (N-methylpyrrolidone) and added to 1 mL NMP solution with 50 μg of black phosphorus quantum dots under nitrogen protection and protected from light. The reaction is carried out at 25° C. under nitrogen protection and protected from light for 12 hours, followed by centrifugation at 7000 to 13000 rpm for 10 to 20 minutes. The supernatant is removed, and the solid is redispersed in ultrapure water, to obtain the titanium ligand-modified black phosphorus. $^1$H-NMR (D$_2$O) thereof is shown in FIG. 2. As seen from FIG. 2, NMR signals of titanium sulfonates are present, indicating the successful coordination of the titanium sulfonate to the surface of black phosphorus.

EXAMPLE 2

A titanium p-toluenesulfonate (TiL$_4$, L: p-toluenesulfonate group) is produced in the same manner as in Example 1. 10.8 mg of titanium p-toluenesulfonate (TiL$_4$, L: p-toluenesulfonate group) is dissolved in 1 mL of DMSO (dimethyl sulfoxide) and added to 1 mL DMF solution with 500 μg multilayered black phosphorous nanosheets under nitrogen protection and protected from light. The reaction is carried out at 40° C. under nitrogen protection and protected from light for 24 hours, followed by centrifugation at 7000 to 13000 rpm for 10 to 20 minutes. The supernatant is removed, and the solid is redispersed in ultrapure water, to obtain the titanium ligand-modified black phosphorus. $^1$H-NMR detection shows that the obtained titanium ligand-modified black phosphorus has NMR signals of titanium sulfonate, indicating the successful coordination of the titanium sulfonate to the surface of black phosphorus.

EXAMPLE 3

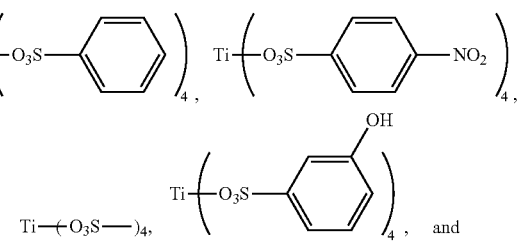

-continued

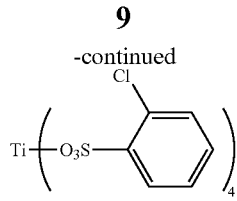

are produced in the same manner as in Example 1, and are coordinated to the surface of black phosphorus in the same manner as in Example 1. NMR data all indicate that the above-mentioned titanium ligands are successfully coordinated to the surface of black phosphorus.

EXAMPLE 4

Stability of the Titanium Ligand-Modified Black Phosphorus

The stability of black phosphorus can be characterized by stable or unstable absorption of its solution in the UV-visible-near infrared region. If its absorption decreases over time, it is indicated to be slowly oxidized, and if its absorption does not decrease over time, it is structurally stable. Black phosphorus is the most unstable in an aqueous solution, and the stability of the titanium ligand-modified black phosphorus (TiL$_4$@BP, wherein TiL$_4$ are

Figure 3:
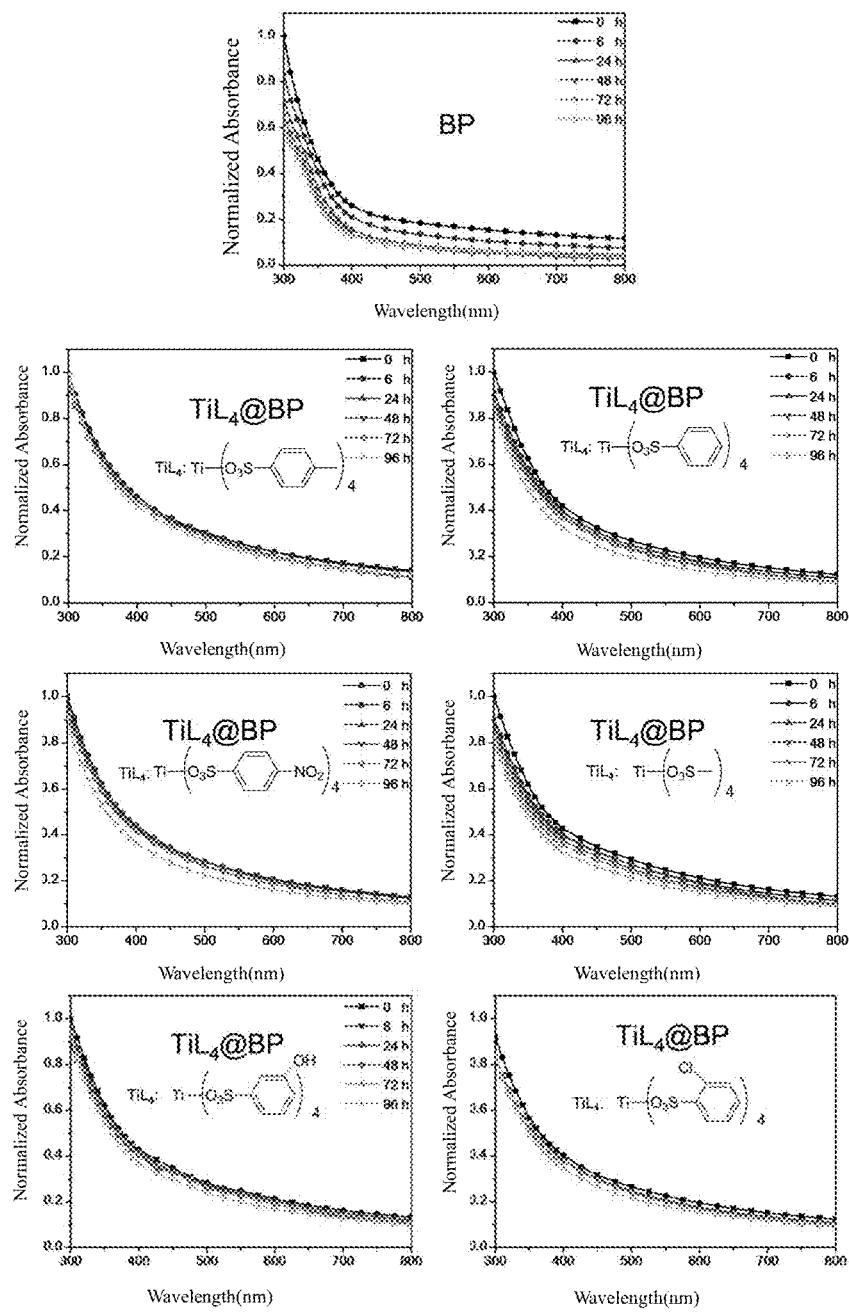
FIG. 3 is a graph of stability test results of an unmodified black phosphorus and a titanium ligand-modified black phosphorus.

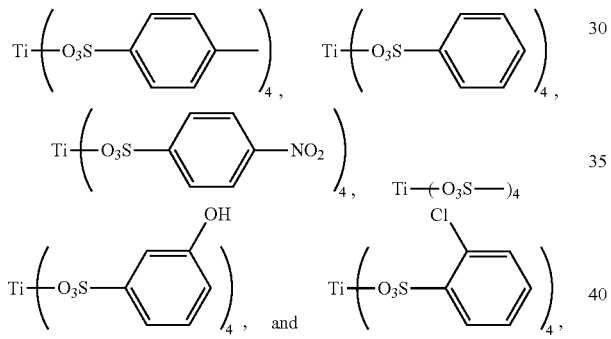

respectively) obtained in Example 1 and Example 3 in the water is studied with the monolayer black phosphorus nanosheet (BP) raw materials of Example 1 and Example 3 as controls. The results are shown in the following FIG. 3. As seen from FIG. 3, the absorption of the monolayer black phosphorus nanosheet raw materials in the aqueous solution decreases over time, and the absorption of the titanium ligand-modified black phosphorus in the aqueous solution is very stable, indicating that the black phosphorus is not likely oxidized after modification with the titanium ligand, and the antioxidant capacity is greatly enhanced.

EXAMPLE 5

Structural Characterization of the Titanium Ligand-Modified Black Phosphorus

The antioxidant property and stability of black phosphorus is enhanced after it is modified with the titanium ligand, but another important requirement for surface modification of black phosphorus is no change in the inherent properties of black phosphorus. In this example, the crystal structures of black phosphorus (BP) and the titanium ligand-modified black phosphorus (TiL$_4$@BP, wherein TiL$_4$ is

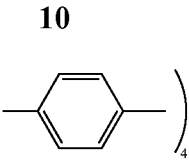

Figure 4:
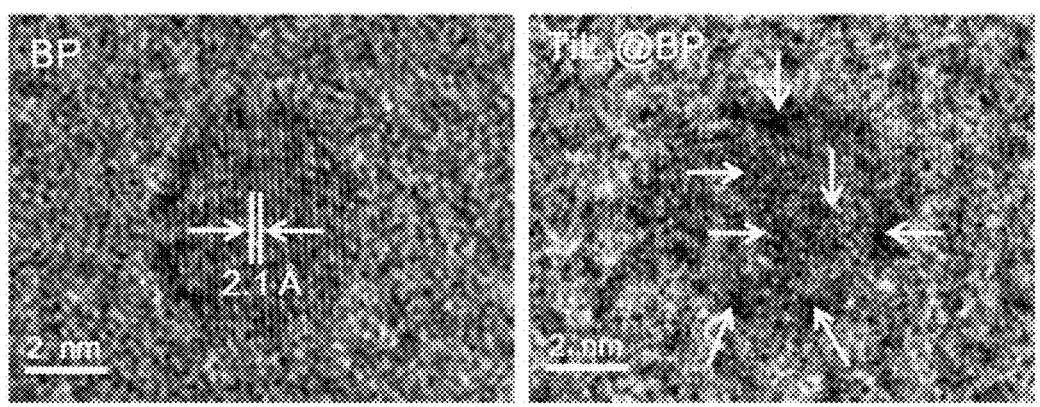
FIG. 4 is a graph of structural characterization of a titanium ligand (TiL$_4$, L: p-toluenesulfonate group)-modified black phosphorus produced in Example 1.

)are studied by a transmission electron microscopy. The study is performed by dropping 4 μL aqueous solution of a sample onto an ultrathin carbon support membrane and observing the crystal structure with a high-resolution transmission electron microscopy after it is naturally air-dried. It is found that the crystal structure of black phosphorus remains before and after the modification with the titanium ligand. As shown in FIG. 4, neat lattice streaks with a width of about 0.21 nm can be observed on the black phosphorus raw material in the high-resolution transmission electron microscope (FIG. 4 (left), streaks reflect the crystal structure of black phosphorus), while these lattice stripes still can be observed on the titanium ligand-modified black phosphorus in the high-resolution transmission electron microscopy (FIG. 4 (right)), indicating that the structure of the black phosphorus is kept. Furthermore, there are black shadows covered above the streaks in some regions, which are the linked titanium ligands.

Finally, it is to be appreciated that the above examples are only illustrative of the implementation and features of the present invention and are not intended to limit the scope of the invention. Although the invention has been described in detail with reference to the above examples, it will be understood by those of ordinary skill in the art that modification or equivalent substitution may be made to the present invention, and any modification or partial substitution made without departing from the spirit and scope of the invention shall fall within the protection scope of the present invention.

The invention claimed is:

1. A titanium ligand-modified black phosphorus, which is a complex of black phosphorus and a titanium ligand having a structure represented by formula (I):

wherein in the formula (I), R$_1$ comprises C$_1$-C$_6$ alkyl, or phenyl optionally further substituted with 0 to 5 groups each independently selected from halogen atom, C$_1$-C$_6$ alkyl, nitro, hydroxy, amino or C$_1$-C$_3$ alkoxy; the C$_1$-C$_6$ alkyl or C$_1$-C$_3$ alkoxy is optionally further substituted with 0 to 3 groups each independently selected from halogen atom, nitro, hydroxy, amino, methyl, ethyl or n-propyl.

2. The titanium ligand-modified black phosphorus according to claim 1, wherein the halogen atom is fluorine atom.

3. The titanium ligand-modified black phosphorus according to claim 1, wherein the titanium ligand comprises:

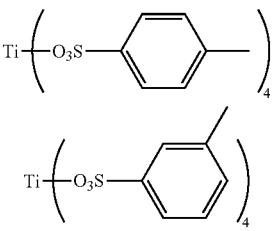

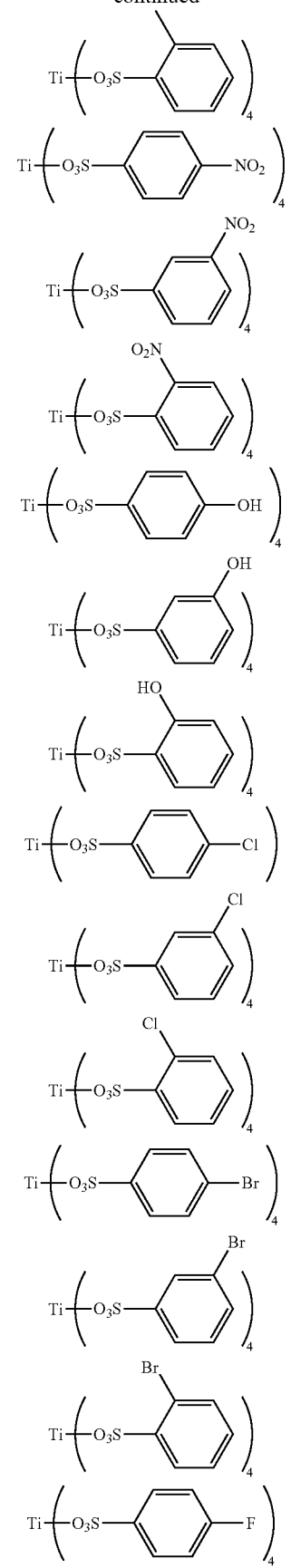
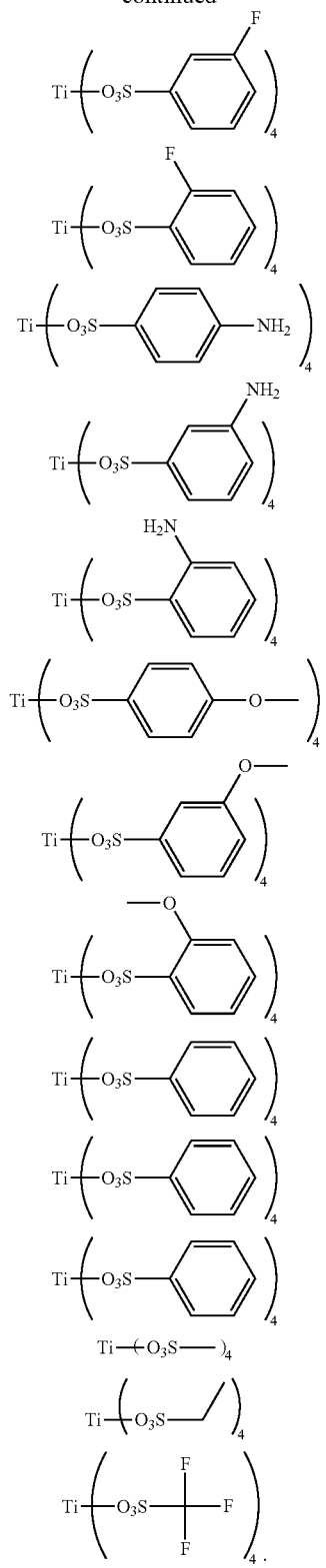
4. The titanium ligand-modified black phosphorus according to claim 1, wherein the black phosphorus comprises one or more of black phosphorous bulk material, multilayered black phosphorous nanosheet, monolayer black phosphorous nanosheet and black phosphorus quantum dot, and wherein the multilayered black phosphorous nanosheet refers to a black phosphorus nanosheet having two or more atomic layers and at a thickness of less than 100 nm.

5. A method of producing the titanium ligand-modified black phosphorus according to claim 1, comprising the steps of:

providing the titanium ligand and the black phosphorus in an organic solvent to take place a reaction protected from light under an inert condition to obtain the titanium ligand-modified black phosphorus.

6. The method according claim 5, wherein the titanium ligand comprises:

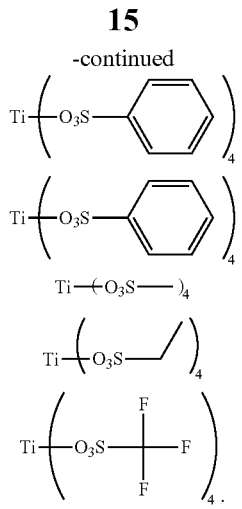

7. The method according to claim 6, wherein the organic solvent comprises polar solvent and/or non-polar solvent, and the polar solvent comprises polar protic solvent and/or polar aprotic solvent.

8. The method according to claim 6, wherein the reaction is carried out at 4 to 45° C. for 12 to 24 h.

9. A composition comprising the titanium ligand-modified black phosphorus according to claim 1.

10. The composition according to claim 9, wherein the halogen atom is fluorine atom.

11. The composition according to claim 9, wherein the titanium ligand comprises:

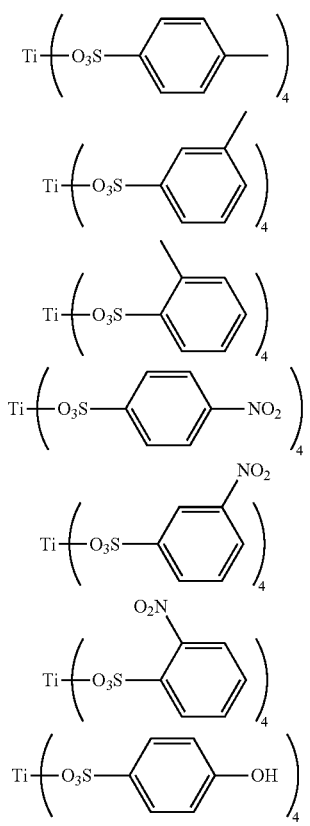

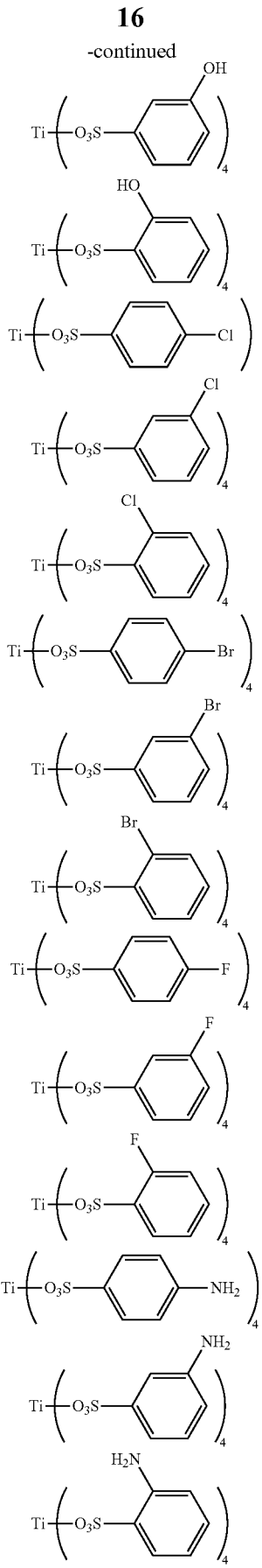

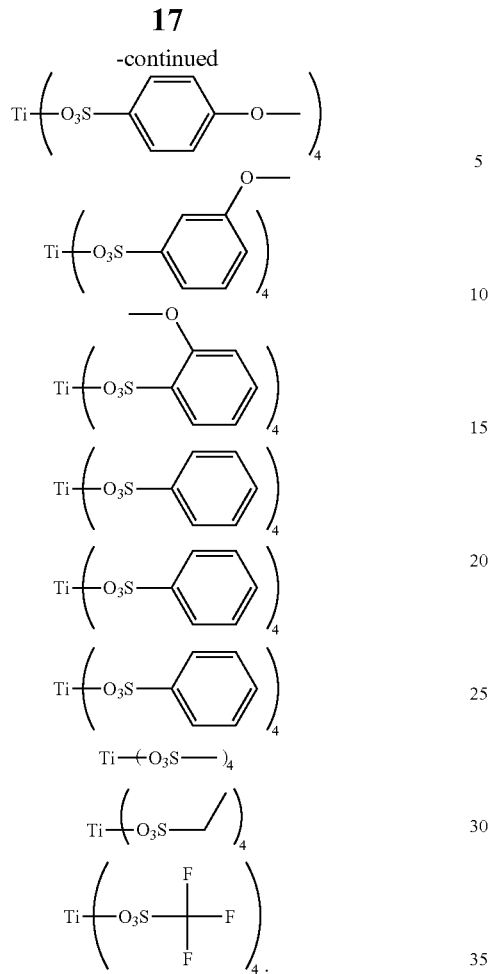

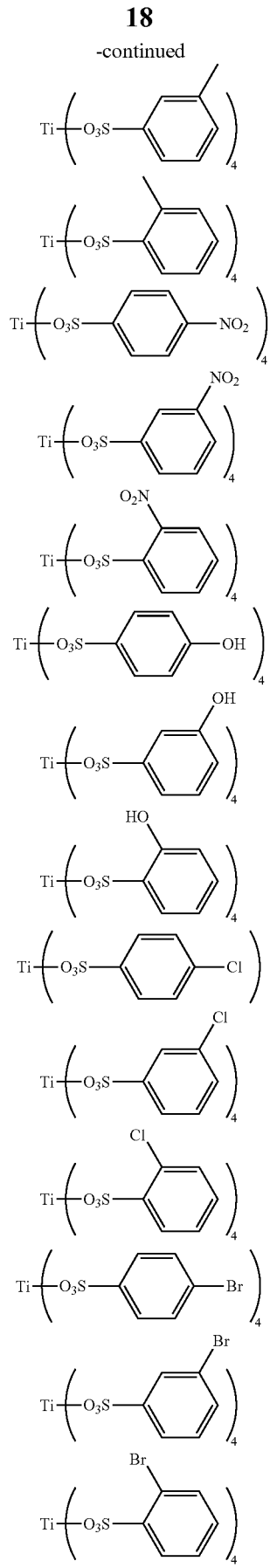

12. A composition according to claim 9, wherein the black phosphorus comprises one or more of black phosphorous bulk material, multilayered black phosphorous nanosheet, monolayer black phosphorous nanosheet and black phosphorus quantum dot, and wherein the multilayered black phosphorous nanosheet refers to a black phosphorus nanosheet having two or more atomic layers and at a thickness of less than 100 nm.

13. A method for preparing materials selected from the group consisting of a thin film transistor material, a negative electrode material for battery, a flexible display material, a LED material, an optical switch material, a biosensor material, a photodynamic therapeutic agent for killing cancer cells and a photothermal therapeutic agent for killing cancer cells, comprising providing the titanium ligand-modified black phosphorus according to claim 1.

14. The method according to claim 13, wherein the halogen atom is fluorine atom.

15. The method according to claim 13, wherein the titanium ligand comprises:

-continued

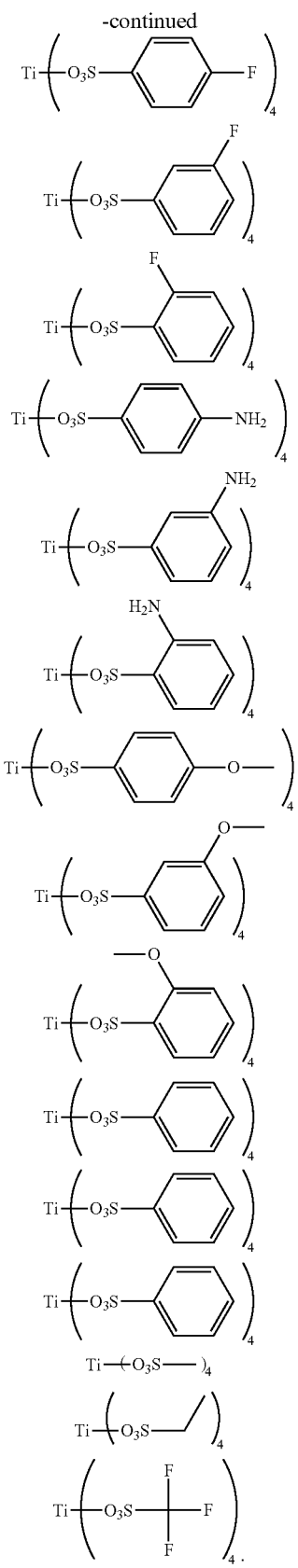

16. The method according to claim 13, wherein the black phosphorus comprises one or more of black phosphorous bulk material, multilayered black phosphorous nanosheet, monolayer black phosphorous nanosheet and black phosphorus quantum dot, and wherein the multilayered black phosphorous nanosheet refers to a black phosphorus nanosheet having two or more atomic layers and at a thickness of less than 100 nm.

17. A method for preparing materials selected from the group consisting of a thin film transistor material, a negative electrode material for battery, a flexible display material, a LED material, an optical switch material, a biosensor material, a photodynamic therapeutic agent for killing cancer cells and a photothermal therapeutic agent for killing cancer cells, comprising providing the titanium ligand-modified black phosphorus composition of claim 9.

18. The method according to claim 17, wherein the halogen atom is fluorine atom.

19. The method according to claim 17, wherein the titanium ligand comprises:

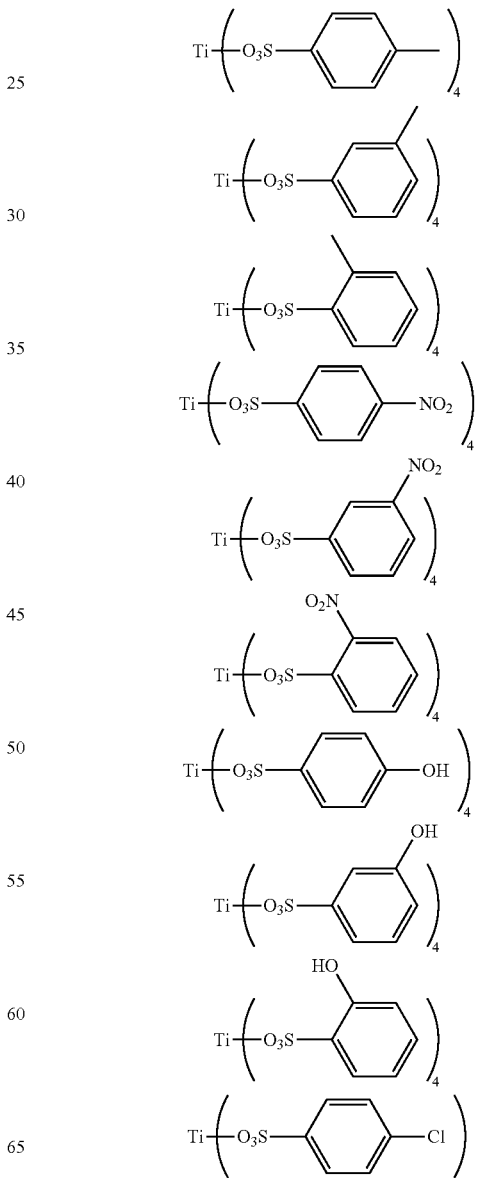

-continued

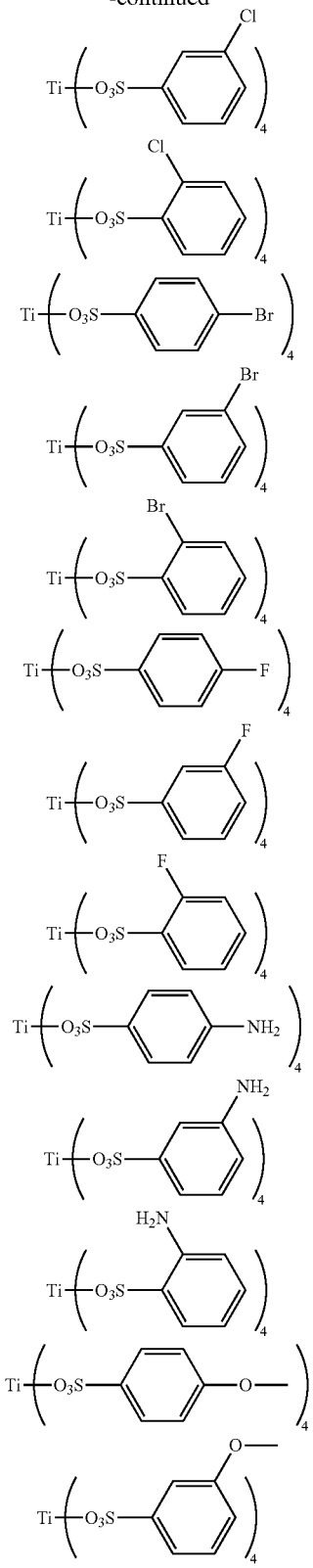

-continued

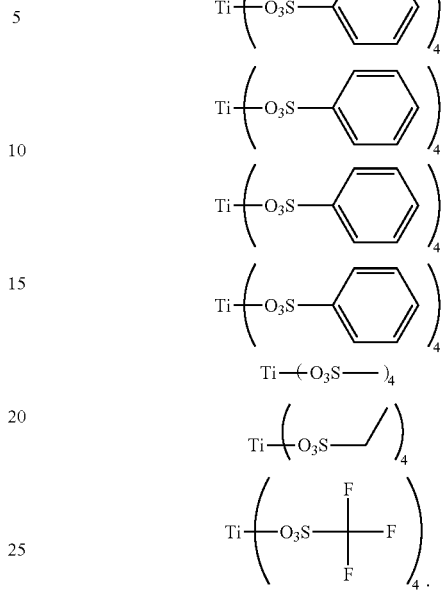

20. The method according to claim 17, wherein the black phosphorus comprises one or more of black phosphorous bulk material, multilayered black phosphorous nanosheet, monolayer black phosphorous nanosheet and black phosphorus quantum dot, and wherein the multilayered black phosphorous nanosheet refers to a black phosphorus nanosheet having two or more atomic layers and at a thickness of less than 100 nm.

21. The titanium ligand-modified black phosphorus according to claim 1, wherein the $C_1$-$C_6$ alkyl is $C_1$-$C_3$ alkyl.

22. The method according to claim 5, wherein the titanium ligand and the black phosphorus are at a molar ratio of between 0.9:1 and 10:1.

23. The method according to claim 22, wherein the titanium ligand and the black phosphorus are at a molar ratio of between 3:1 and 10:1.

24. The method according to claim 7, wherein the polar aprotic solvent comprises one or more of N-methylpyrrolidone, N,N-dimethylformamide, N,N-diethylformamide, N,N-dimethylacetamide, dimethylsulfoxide, tetrahydrofuran, ethyl acetate and acetone.

25. The method according to claim 7, wherein the polar protic solvent comprises one or more of methanol, ethanol, n-propanol, isopropanol, ethylene glycol and butylene glycol.

26. The method according to claim 7, wherein the nonpolar solvent comprises methylene chloride and/or trichloromethane.

* * * * *